(12) United States Patent
Singh et al.

(10) Patent No.: US 10,553,504 B2
(45) Date of Patent: Feb. 4, 2020

(54) INSPECTION OF SUBSTRATES

(71) Applicant: Rudolph Technologies, Inc., Wilmington, MA (US)

(72) Inventors: Gurvinder Singh, Corcoran, MN (US); Wu Y. Han, Plano, TX (US); John Thornell, McKinney, TX (US); Chetan Suresh, Bloomington, MN (US); Wayne Fitzgerald, Andover, MA (US)

(73) Assignee: Rudolph Technologies, Inc., Wilmington, MA (US)

( * ) Notice: Subject to any disclaimer, the term of this patent is extended or adjusted under 35 U.S.C. 154(b) by 0 days.

(21) Appl. No.: 15/933,366

(22) Filed: Mar. 22, 2018

(65) Prior Publication Data
US 2018/0277452 A1 Sep. 27, 2018

Related U.S. Application Data (60) Provisional application No. 62/475,020, filed on Mar. 22, 2017.

(51) Int. Cl.
| | |
|---|---|
| *H01L 21/66* | (2006.01) |
| *G01N 21/64* | (2006.01) |
| *G01N 21/95* | (2006.01) |
| *H01L 21/02* | (2006.01) |

(52) U.S. Cl.
CPC .......... *H01L 22/20* (2013.01); *G01N 21/64* (2013.01); *G01N 21/9501* (2013.01); *H01L 21/02068* (2013.01)

(58) Field of Classification Search
CPC ...................................................... H01L 22/20

USPC .......................................................... 438/4
See application file for complete search history.

(56) References Cited

U.S. PATENT DOCUMENTS

| | | | |
|---|---|---|---|
| 4,681,442 A | 7/1987 | Wagner | |
| 5,208,648 A | 5/1993 | Batchelder et al. | |
| 2003/0223536 A1* | 12/2003 | Yun | B82Y 10/00 378/45 |
| 2006/0139627 A1* | 6/2006 | Lin | G01N 21/8806 356/237.1 |
| 2007/0098249 A1* | 5/2007 | Miyano | G06K 9/32 382/145 |
| 2012/0126141 A1 | 5/2012 | Pulisciano et al. | |
| 2015/0192529 A1 | 7/2015 | Sato et al. | |
| 2016/0097983 A1* | 4/2016 | Bogaart | G03F 7/70625 250/372 |
| 2018/0254597 A1* | 9/2018 | Van Der Post | H01S 3/0959 |

OTHER PUBLICATIONS

Pollard, Kimberly et al., "Characterization of Clean After Photoresist Removal From Wafers With Copper Pillars With Lead Free Solder Caps", presented at IMAPS Device Packaging, Phoenix, Arizona; Mar. 15, 2006, 4 pages.

* cited by examiner

*Primary Examiner* — Jami Valentine Miller
(74) *Attorney, Agent, or Firm* — Todd R. Fronek; Larkin Hoffman Daly & Lindgren, Ltd.

(57) ABSTRACT

Concepts presented herein relate to approaches for performing substrate inspection. In one aspect, the concepts relate to detecting anomalies or candidate defects on the substrate based on contrast in images obtained of the substrate.

17 Claims, 5 Drawing Sheets

Fig. 7D

INSPECTION OF SUBSTRATES

BACKGROUND

Current inspection of electronic devices such as wafers, circuit boards, flat panel displays, multichip modules and high-density packages use several different inspection techniques. These inspection techniques can be used during various times in the manufacturing process in order to identify various conditions associated with manufacturing of the devices.

SUMMARY

Concepts presented herein relate to approaches for performing substrate inspection. In one aspect, the concepts relate to detecting anomalies or candidate defects on the substrate based on contrast in images obtained of the substrate.

DETAILED DESCRIPTION

Figure 1:
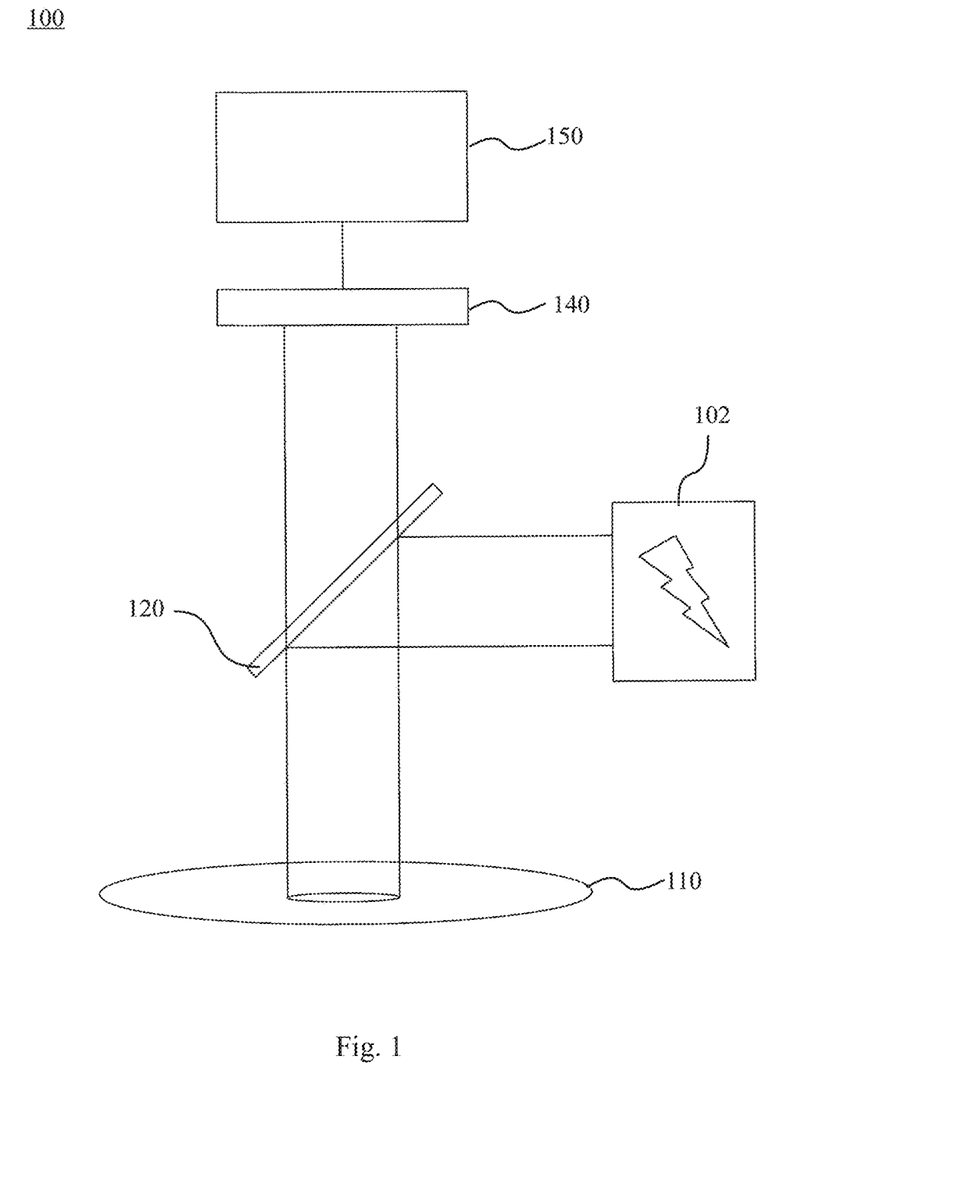
FIG. 1 is a schematic diagram of an example optical system.

As schematically illustrated in FIG. 1, an optical system 100 includes a light source 102 provided to illuminate a substrate 110. As used herein, the term 'light' is intended to encompass all forms of electromagnetic radiation at any useful wavelength or wavelengths. An excitation light (e.g., ultraviolet) from the light source 102 is transmitted to a filter and beam splitter 120 which passes and reflects different wavelengths of light. The beam splitter 120 reflects the excitation light from the source 102 onto the substrate 110. Portions of the substrate 110, for example, non-fluorescent metal leads and non-metallic layers, reflect light impinging thereon. Light reflected from these portions of the substrate 110 maintains the same wavelength as the excitation light from the source 102. In some embodiments, the excitation light from the source 102 is in the ultraviolet range of wavelengths. But because the beam splitter 120 reflects the excitation light from the source 102, light returned from the source at the incident wavelength is reflected from the beam splitter 120 and away from a sensor 140.

Some of the excitation light from source 102 is incident on materials, e.g. organic materials, which fluoresce upon absorbing light at an excitation wavelength. This phenomenon is well known to those skilled in the art. Generally, the wavelength of the fluorescent light emitted from the substrate is of a longer wavelength than the excitation light, however this is not always the case. The optical system 100 then, must separate excitation light from the source 102 from the fluorescent light emitted from the substrate so that the fluorescent light may be incident upon a sensor 140. This is done by filtering light returned from the substrate using a wavelength sensitive filter or more preferably, by using a wavelength specific beam splitter 140. In a preferred embodiment the beam splitter is dichroic, reflecting light at one range of wavelengths and passing light at another range of wavelengths. This type of beam splitter can be set up as a long pass filter, short pass filter, or a band pass filter. Of particular interest are beam splitters that will pass fluorescent light, but reflect excitation light.

Optical system 100 can include several different optical components as desired to capture images of substrate 110. These components are not illustrated for clarity and brevity reasons, but may include lenses, collimators, beam splitters, filters, etc. for focusing, collection and collimation of light. Additionally, optical system 100 can include different light sources (which may not be shown) and sensors configured to capture various types of images as desired. Light source 102 may emit light in a single wavelength or a narrow band of wavelengths (e.g. monochromatic) or across a wider band of wavelengths that is exclusive of the wavelengths of fluorescent light that is of interest. Source 102 may include an incandescent or fluorescent bulb or may constitute one or more LED's. Lasers may also be used. While the example shown in the figures is of a simple brightfield imaging arrangement, alternative optical techniques darkfield and interferometry are also contemplated.

In accordance with one example embodiment of optical system 100, excitation light is absorbed by material on the substrate, the material fluorescing as a result. In this example embodiment, the light emitted by the foreign material has a wavelength which is longer than the excitation source light, which is in this embodiment in the ultraviolet range. For example, the emitted light may be in the visible light spectrum. The fluorescent light that is emitted from the substrate in the direction of the beam splitter 120 is transmitted through the beam splitter 120, which in this instance acts as a long pass filter.

Light which is transmitted through the beam splitter 120 is directed to the sensor 140, through other optical components such as lenses, filters, etc. In one embodiment, the sensor 140 is a time delay integration (TDI) camera, area scan camera, hyperspectral camera or other sensor type (e.g., one that captures color information) as desired. These sensors may be of a CCD or CMOS arrangement, as desired. The sensor 140 is coupled to a controller 150. The controller 150, in one embodiment, includes a computer, I/O facilities to couple the sensor 140 to the computer, a processor, memory, and optionally network capabilities that allow the controller 150 to be connected to other local or remote controllers or to a computer network over which instructions are received and data is sent. The controller 150, in one embodiment, controls imaging and image processing related to operation of the optical system 100.

Controller 150 may also control mechanisms (e.g., a stage and/or a robot), to coordinate automated handling and processing of substrates. The controller 150 can work in local mode, handling all operations on the local system or can distribute some of its functions to remote controllers. An equipment front end module (EFEM) or other handler (not shown) can be coupled to a separate controller that coordinates the provision and removal of substrates from a stage. The stage can be controlled by a motion controller that may be separate from, but which works in conjunction with, controller 150.

Example functions performed by the controller 150 include obtaining raw image data from the optical system 100 (e.g., from sensor 140) and producing data relevant for image analysis. Various different analytical processes utilized by controller 150 include, for example, identifying anomalies, forming overlay images, classifying defects, analyzing thresholds, analyzing wafer yield and analyzing capture selection for images of the substrate. Given these analyses, various actions can be implemented, including performing further substrate processing steps, modifying substrate production processes, discarding substrates, approving substrates and/or approving a portion of substrates.

Alternatively, or in addition thereto, metallic materials on the substrate do not fluoresce and typically produce a grayscale value of zero or near zero when exposed to ultraviolet light. If a layer of non-metallic material is positioned on top of the metallic layer, the resulting grayscale value will be greater than zero.

In one example, optical system 100 can be useful in identifying candidate defects, i.e. anomalies. For example, the candidate defects can indicate potential electrical failure on a surface of a substrate. In one embodiment, once a candidate defect is identified by optical system 100, a second optical processing technique can be used, such as dark field illumination or interferometry in order to provide further information as to whether the candidate defect is likely to cause failure of a device, can be removed and/or is merely a nuisance defect and can be ignored.

Figure 2A:
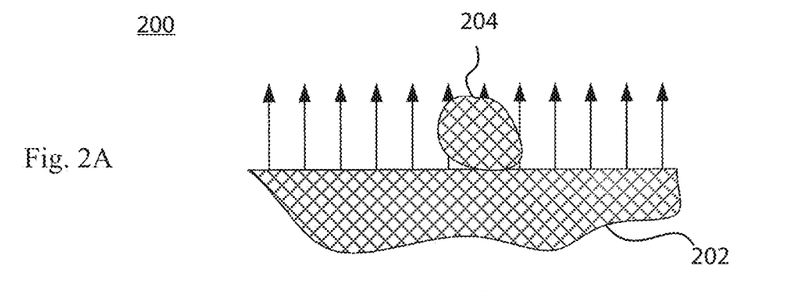
FIG. 2A is a schematic illustration of a candidate defect positioned on a metallic layer.
Figure 2B:
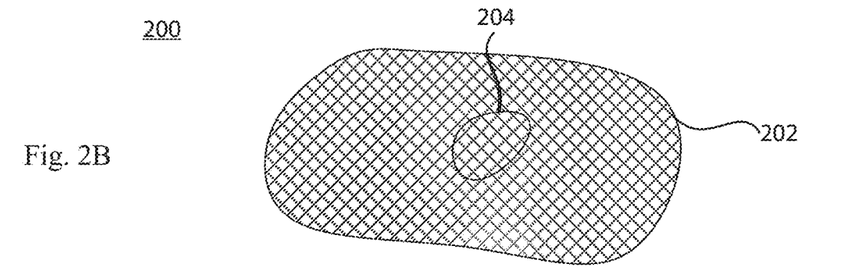
FIG. 2B is a schematic illustration of a top view of a candidate defect positioned on a metallic layer.

FIG. 2A illustrates an example area of interest (AOI) of a substrate 200 having a metallic layer 202 having a candidate defect 204 (herein illustrated as a metallic nodule) positioned thereon. In one embodiment, the metallic layer 202 is an electrical lead of a semiconductor device. In this example, the candidate defect 204 is a metallic nodule defined with a particular height H extending above a top surface of the metallic layer 202. Typical imaging techniques such as visible wavelength brightfield imaging often have difficulty in distinguishing between the metallic layer 202 and the candidate defect 204. There is little contrast in intensity of light reflected from a top of metallic layer 202 and a top of candidate defect 204. For example, FIG. 2A schematically illustrates arrows indicative of intensity reflected from metallic layer 202 and candidate defect 204. Moreover, FIG. 2B schematically illustrates a top image of the candidate defect 204 and surrounding metallic layer 202, wherein limited contrast exists between the candidate defect and surrounding metallic layer. Fluorescence imaging systems can have difficulties with candidate defects 204 such as those illustrated in FIGS. 2A and 2B as the metal from which these objects are formed does not fluoresce. Accordingly, the sensor 140 will record very dark images that have a very low contrast; this makes it very difficult to discern the presence of a candidate defect 204.

Figure 2C:
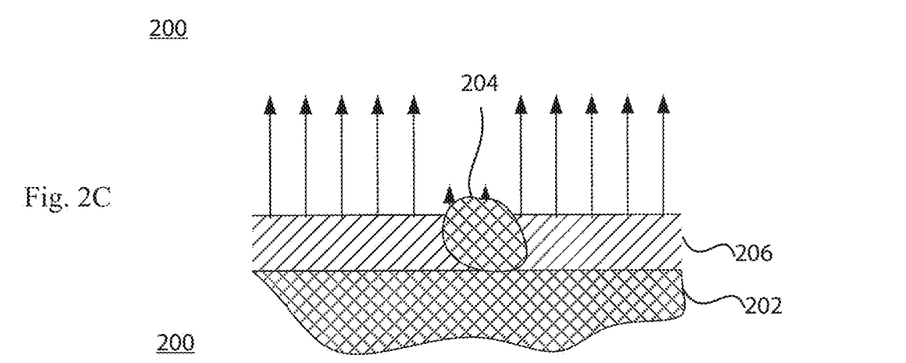
FIG. 2C is a schematic illustration of a candidate defect positioned on a metallic layer and protruding from a non-metallic layer.

Depending on the height H of the candidate defect 204, the defect may cause an electrical failure or other issue that will create a device failure if not removed. However, in other situations, the height H of the candidate defect 124 can be such that it is unlikely to cause an electrical failure. As schematically illustrated in FIG. 2C, the candidate defect 204 protrudes from a non-metallic (e.g., a dielectric or passivation coating) layer 206. A fluorescent image of the AOI 200 illustrated in FIG. 2C will produce an image with varying intensity. In particular, fluorescent light emitted by layer 206 will have a larger intensity (schematically shown by longer arrows in FIG. 2C) than light returned from the candidate defect 204 (schematically shown by shorter arrows in FIG. 2C) as the arrangement of the optical system 100 filters out any light that might be returned from the non-fluorescent metallic candidate defect 204. An image captured by the sensor 140 shows a bright layer 206 surrounding a dark candidate defect 204 with sufficient contrast between the layer and the candidate defect to reliably resolve the candidate defect 204.

Figure 2D:
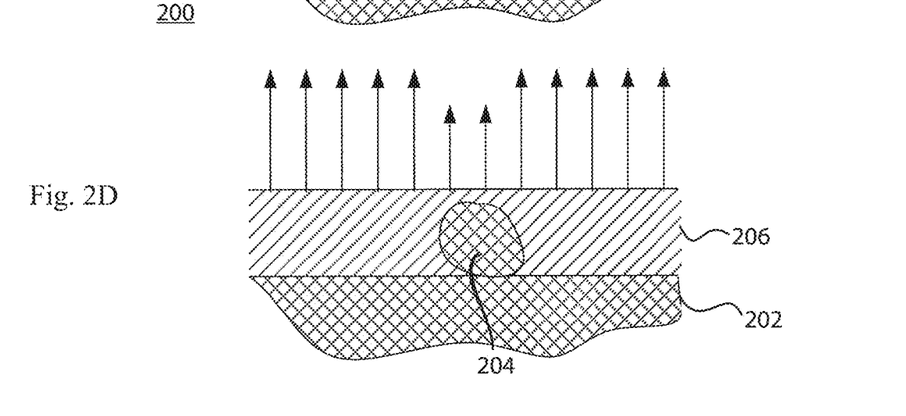
FIG. 2D is a schematic illustration of a candidate defect positioned on a metallic layer and covered by a non-metallic layer.

FIG. 2D schematically illustrates another scenario where non-metallic, fluorescent layer 206 is of a height to completely cover the candidate defect 204. In this scenario, images of a top of the AOI 200 will still vary in intensity. As schematically illustrated in FIG. 2D, light emitted from layer 206 because of fluorescence will have a larger intensity where there is no candidate defect present and have a smaller intensity where candidate defect 204 is present.

Figure 3:
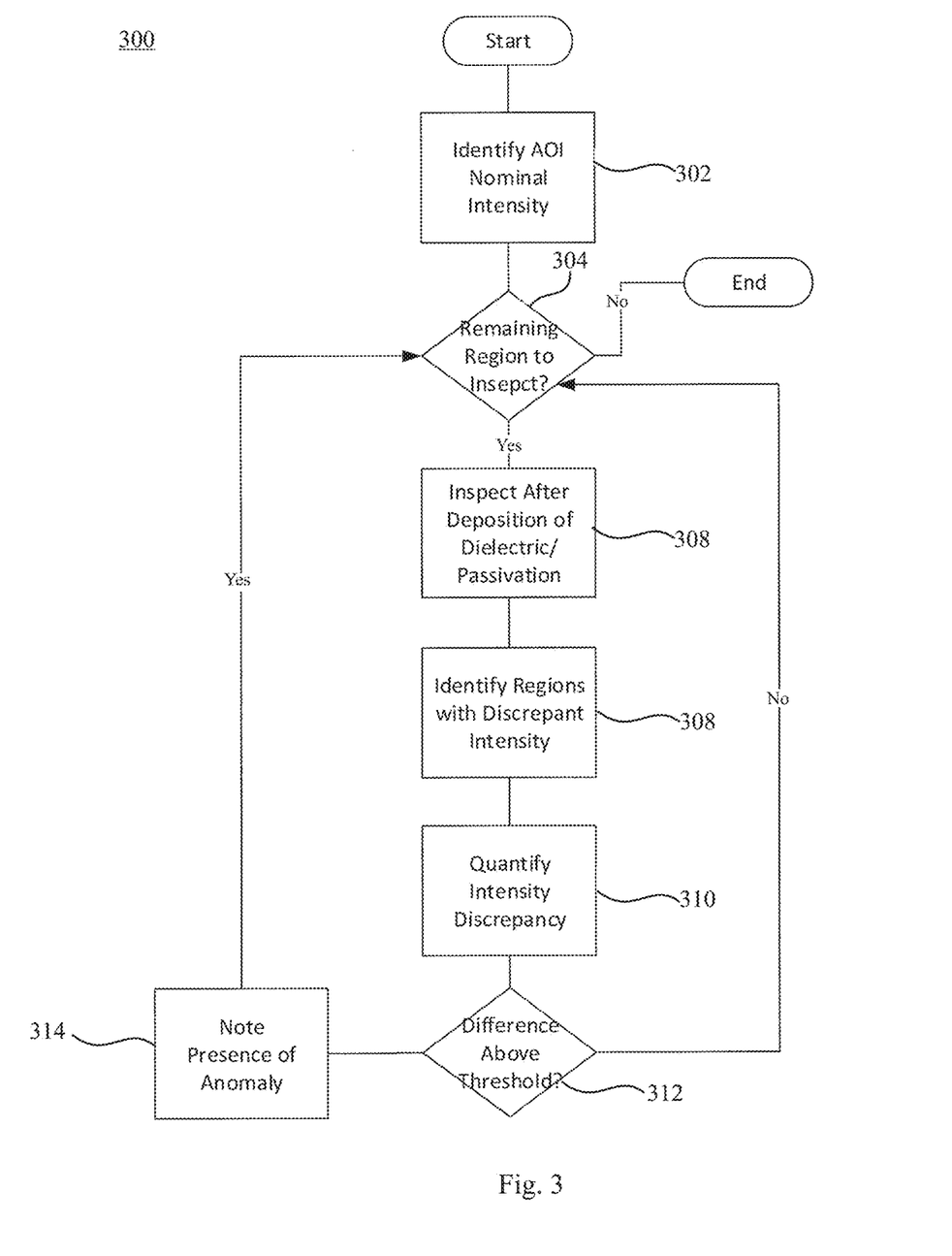
FIG. 3 is a flow diagram of a method for inspecting a substrate.

FIG. 3 is an example flow diagram of a method 300 for inspecting a substrate as discussed above. Step 302 includes identifying an area of interest nominal intensity. The nominal intensity can be identified, for example using a model based on a fluorescent material characteristic or based on multiple images of similar areas of interest. As discussed above, metallic areas will have a lower nominal intensity, while fluorescent, non-metallic areas will have a higher nominal intensity. Given the nominal intensity identification, inspection for regions of the substrate can be identified and a determination is made as to whether regions for inspection remain at step 304. After deposition of a non-metallic dielectric or passivation layer, a particular region is inspected at step 306. The inspection takes place using optical system 100 as discussed above.

Given the inspection conducted at step 306, regions with discrepant intensity are identified at step 308. This identification can be conducted by comparing the information received during the inspection at 306 and the nominal intensity identified at step 302. Given the comparison, the intensity discrepancy can be quantified in several different ways. In one example, a number of pixels that differ in the particular region between the inspection image and model can be selected as the quantification of the discrepancy. In other examples, the quantification can be selected as a difference in grayscale value for pixels in the particular region. Regardless of the particular quantification, a difference value can be compared to a particular threshold at step 312. If the difference is below the threshold, no anomaly or candidate defects are detected and method 300 returns to step 304. If the difference is above the threshold, method 300 proceeds to step 314, where a presence of an anomaly or candidate defect is noted. Method 300 then proceeds to step 304. If further regions remain to be inspected, method 300 repeats steps 306-312 for additional regions. If there are no regions left to be inspected, method 300 ends.

Based on the presence of one or more anomalies on a substrate further processing techniques can be employed. For example, additional optical techniques can be used on various regions that include anomalies so as to provide a likelihood that a candidate defect will cause an electrical failure. In one example, a region can be inspected using dark field illumination based on a position of the candidate defect. Using dark field illumination, the height of the candidate defect can be calculated. In one example, a particular threshold can be selected such that if the height of the candidate defect is greater than a selected threshold, it will be more likely that the resulting semiconductor device will fail, whereas if the height is below the threshold, the candidate defect will be unlikely cause an electrical fail. Given the extent of the height calculation, further processing techniques can then be determined, such as cleaning the semiconductor device, approving the semiconductor device for further processing, discarding the semiconductor device and others.

Figure 4:
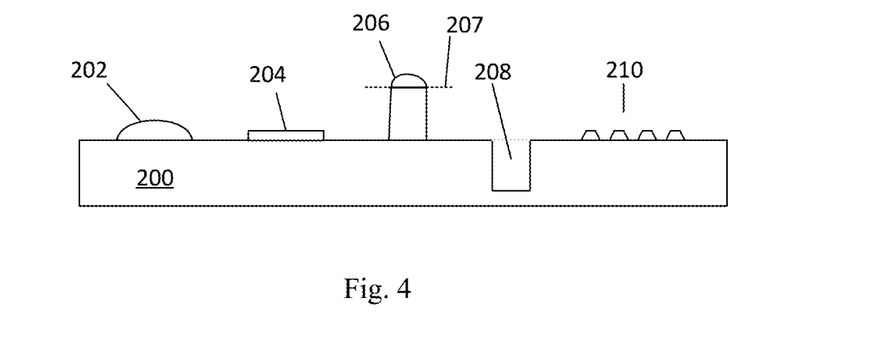
FIG. 4 is a schematic side view of some structures that are present on a semiconductor substrate.

FIG. 4 illustrates a number of structures on a substrate 200 that may be inspected. In this case the substrate 200 is a semiconductor substrate of silicon, sapphire, silicon on insulator (SOI), epoxy, glass, plastic, or any other conventional material on which semiconductor devices are formed or assembled. On the left side of the substrate 200 is a 'bump' 202, which is a small quantity of solder, gold or other suitable conductive material that extends above the surface of the substrate 200. A bump 202 is emplaced on a substrate 202 to form one portion of an electrical connection between a device that is on or incorporated into the substrate 200 and another device (not shown). This connection may be mechanical or a solder connection.

To the right of the bump 202 is a pad 204. A pad 204 is fairly similar to a bump 202 but generally differs in the height. The pad 204 is the structure that is directly connected to a device (e.g., an integrated circuit (IC) device) on the substrate 200. What is more, bumps 202 are often formed on top of pads 204. Electrical connections to a pad 204 are generally mechanical or soldered.

Pillar 206 is a variation on the bump 202 and pad 204. Pillars are formed of conductive materials such as copper and may have a solder cap on their top. Pillars 206 have a greater height as in later processing steps the pillar 206 may be largely buried by layers of material deposited around the pillar 206. The height of the pillar 206 allows an electrical connection to be formed by mechanical or soldered means once material has been deposited around the pillar 206 as suggested by dashed line 207.

A via 208 is a bore formed into a substrate 200. The via 208, once filled with a conductive material such as copper, allows electrical connections to be made through layers of an IC device or even through the substrate 200 itself. The empty via 208 shown in the Figure may also become a pillar 206.

Traces 210 are linear conductors formed on the surface of the substrate 200. These traces are formed of conductive materials such as, for example, copper. Traces 210 connect various structures within an IC device or between IC devices.

Figure 5:
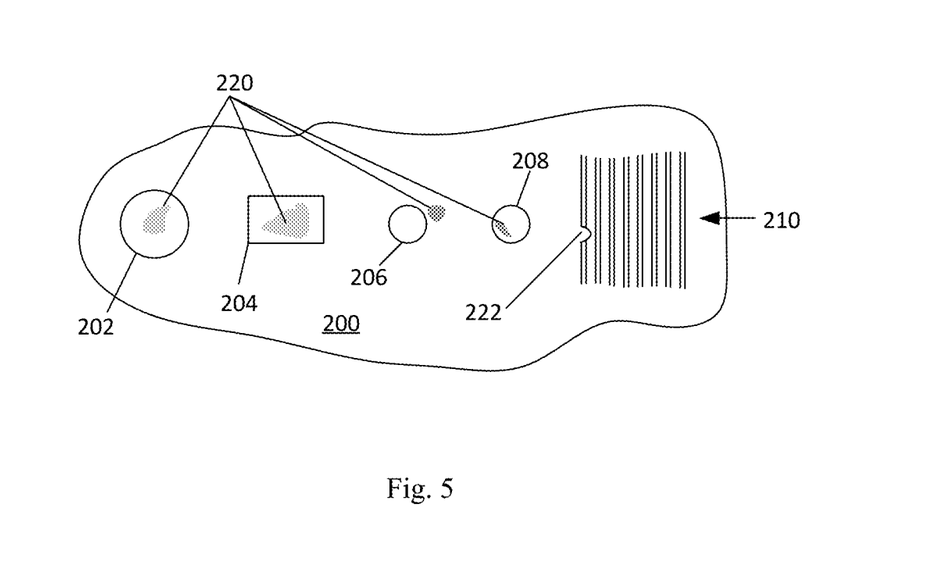
FIG. 5 is a plan view of the structures illustrated in FIG. 4.

A common feature of the structures formed on or in substrate 200 is that they are all formed of materials that are conductive and which do not fluoresce. Another common feature is that various types of materials that can be deposited on these structures can cause problems with the formation of electrical connections to these structures. As seen in FIG. 5, contaminants 220 can sometimes be found on or adjacent to such structures formed on substrate 200. Further, contaminants can also prevent the material of a structures such as trace 210 from adhering to the structure 200 as shown by gap 222 in trace 210. Of interest here is that many contaminants fluoresce when exposed to selected excitation wavelengths. The difference in the way conductive materials (metals) and contaminants (often organics) react to excitation wavelengths is helpful in identifying defective IC devices or discrepant processes used to form such devices.

In one embodiment, a structure (e.g., structures 202-210) on a substrate 200 is defined as a region of interest, that is, a portion of the substrate 200 that will be assessed for the presence of defects or contaminants. As described above, an image of a substrate 200 is captured, wherein the substrate 200 is illuminated using selected excitation wavelengths. Filters of one sort or another are used to block light in the excitation wavelengths from reaching the sensor 140. The image captured by the sensor 140 and reported to the controller 150 is therefore largely composed of light from fluorescent contaminants. Where contaminants 220 are determined to be on top of a structure such as bump 202 or pad 204 or inside a via 208, those structures are considered to be defective as the presence of contaminants 220 may hinder the formation of electrical connections. Similarly, where a contaminant 220 overlies a trace 210 or has resulted in a gap in a trace 210, then that trace 210 may also be considered to be defective. While contaminants 220 on a substrate 200 are to be avoided as general rule, the presence of contaminants 220 adjacent a structure such as pillar 206 may be acceptable insofar as they should not hinder the formation of electrical connections with the pillar 206.

Figure 6A:
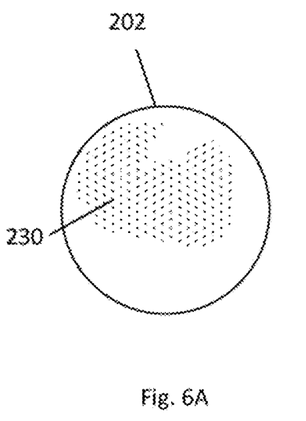
FIGS. 6A-6C are schematic illustrations of anomalies identified on a substrate at different wavelengths.
Figure 6B:
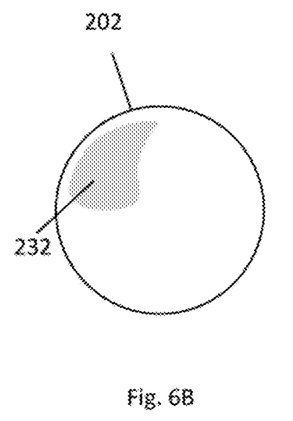
Figure 6C:
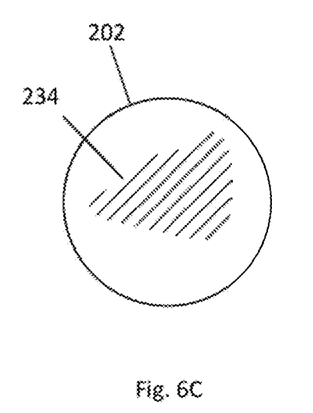

In some situations, more than one type of contaminant may be present on a structure. FIGS. 6A-6C schematically illustrate one such example. In FIG. 6A a bump 202 is shown as having large area 230 that is contaminated. For purposes of this description, the area 230 is shown in FIG. 6A as it might appear in a standard brightfield microscope image. Note that the area 230 is undifferentiated in this image, i.e. it is a large, seemingly uniform object. Taking advantage of the fact that different materials fluoresce at different wavelengths the area 230 of contamination may be seen to comprise two different types 232, 234 of contamination. This type of imaging is accomplished by ensuring that illuminator 102 outputs excitation wavelengths of light associated with the fluorescence of the different types 232, 234 of contamination. Such an illuminator 102 may be a single wide or broad band illumination source or a series of individual, essentially monochromatic sources that are coupled into the optical path. Of the system 100. In some instances it is possible that a single wavelength of excitation light may be sufficient to excite fluorescence in both types 232, 234 of contamination.

Light incident upon sensor 140 may be filtered to pass only that wavelength of light that is emitted by the respective types 232, 234 of contamination. This can be done at successive wavelengths such that separate images of the types 232, 234 of contamination are obtained. Alternatively, a hyperspectral or other 'color' sensor 140 capable of parsing multiple wavelengths at one time may be used. To simplify, if the sensor 140 is monochromatic, then the illuminator will be cycled through each wavelength of excitation light to ensure that there is a one to one relationship between the type and the wavelength of excitation light. Where excitation light is mixed or does not have a one to one relationship with the type of contamination, then the light incident upon the sensor 140 may be filtered, using a beam splitter or a succession of filters interposed into the optical path between the object and the sensor 140. In a preferred embodiment, multiple excitation wavelengths may be used and multiple fluorescence wavelengths sensed, all at one time.

Inspection of substrates 200 generally involves the capture of an image and the comparison of that image with a model or even another image that is nominally identical. This comparison results in a difference image, which is a nominal image showing the differences between the two compared images. The information in this difference image is then assessed to determine whether differences or anomalies are defective or not. This assessment, also often referred to as segmentation, is conducted on all of the information in the difference image. Where a substrate 200 has a high degree of variability segmentation criteria may identify far more defects than actually exist, i.e. false positives may be identified.

One technique often used in the past is to binarize the difference image to eliminate weak or marginal signals. Binarization is the process of assessing each pixel of an image as having a high value (e.g. 256 intensity) or a low value (e.g. 0 intensity) on the basis of whether each pixel in the difference image has an initial value above or below a predetermined threshold. This threshold may be based on a heuristic or may be based upon verification of whether identified defects were real or false. One problem with this is that binarization used at the difference image stage can limit what types of data are usable for comparison.

One solution is to use binarization on captured images directly before comparison with a model, with other images, or even with non-image data such as computer aided design (CAD) data. One benefit of fluorescence imaging is that since most of the light from which the image is formed is from a small number of discrete materials, the images obtained tend to be much simpler than those captured in normal microscopy. For example, color and monochromatic images of metallic structures at high resolution often reveal a blotch appearance. This appearance may be the grain structure of the metallic materials themselves, or some surface characteristic that is the result of the fabrication process. This blotch appearance tends to throw up a large number of false positive defects, while simultaneously obscuring defects that may exist in or on those metallic structures. An image of a metallic structure obtained using fluorescence imaging techniques is uniformly dark as metals do not fluoresce, except where a contaminant is present. A model formed by combining highly variable images is difficult to use as the standard deviation for such models may be too large to usefully indicate the presence of a defect. Similarly, direct comparison of two highly variable images does not provide much useful information as there is little information contained in the resulting differences, i.e. there is far too much noise in the difference image to obtain a useful comparison.

Figure 7A:
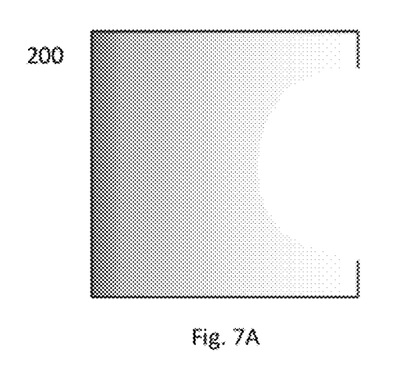
FIGS. 7A-7D illustrate schematically an image processing technique for identifying anomalies on a substrate.
Figure 7B:
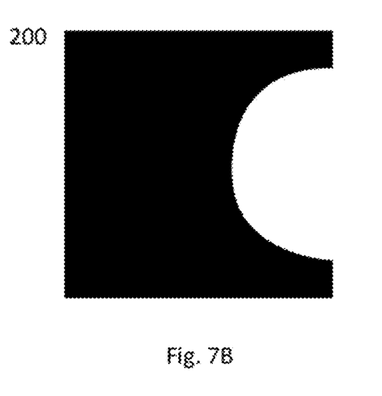

In one embodiment of the present concepts, an image of a structure on a substrate is captured and then binarized before any comparison is conducted. In FIG. 7A, the substrate 200 shows an intensity gradient that moves from high intensity (dark) to low intensity (light) from left to right. Further, an anomaly 236 that is marginally lighter than the substrate 200 can be seen in the right side of the substrate 200. Applying a binarization step to the image of FIG. 7A results in FIG. 7B. Here, every pixel that was above a predetermined threshold was marked as high (in this instance, black) and every pixel that was below threshold was marked as low (white). This has the effect of removing the variability represented by the gradient in the image shown in FIG. 7A. FIG. 7B is a literal black and white representation of the substrate 200 on a few levels. First, the image is monochromatic. Second, ambiguity has been reduced. It is noted that the reduction of ambiguity in FIG. 7B may have removed some information related to the substrate 200, but the simplification is helpful in terms of conducting an inspection of that substrate.

Figure 7C:
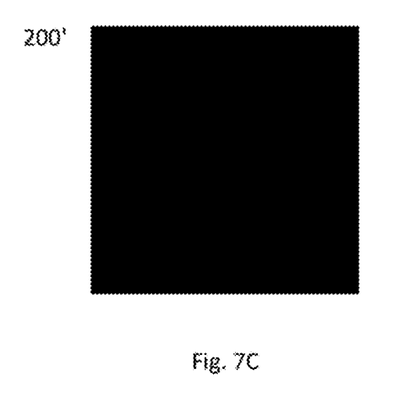
Figure 7D:
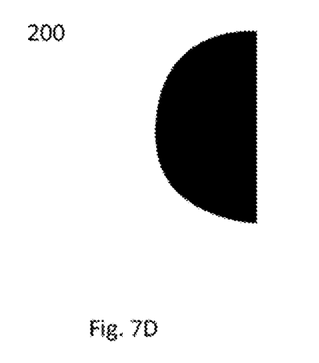

FIG. 7C is a representation of an ideal substrate 200', also binarized. Note that in some instances this representation may be derived from a statistical model of a substrate, from an actual image of a nominally identical substrate, or more interestingly, from CAD data pertaining to the substrate. Direct comparison between the ideal substrate 200' and the binarized image of FIG. 7C results in an unambiguous image of the anomaly alluded to in relation to FIG. 7A. This anomaly may then be assessed or segmented to determine if it is a defect.

The inspection of substrates and in particular semiconductor substrates has as one of its purposes the improvement of yield and its related value, profit. Inspection identifies those substrates or individual devices that have defects that are well correlated with poor functionality. In some cases it is sufficient to identify such defective substrates or individual devices and to discard them without further processing. In other instances, it is possible to redirect or modify the processing of defective substrates to improve the yield. For example, substrates shown to have problematic contaminates on their surface can be subjected to additional cleaning to remove such contamination. Subsequent inspection will verify whether this additional step has been effective. Subsequent inspection may be used to subject a substrate to alternative processes where a prior process has proven to be less than effective. For instance, a cleaning process using deionized water may not remove one or more types of contamination on a substrate. A subsequent inspection step may be used to identify the ineffectiveness of the previous cleaning step and a different cleaning step using, for example microwaves, may be selected. As always, a financial consideration controls how substrates are disposed. Where extra or alternative processing steps commercially infeasible, then the presence of problematic defects such as contaminants will result in the scrapping of these substrates. Financial considerations may also dictate the use of one type of subsequent processing over another. Again using the example of the cleaning of contaminants from a wafer, one may determine that an slightly less effective, though more inexpensive, cleaning process may be preferable to the use of a more effective, but more expensive, cleaning process where the cost differential between the two processes exceeds the gain obtained from an increased yield. Alternatively, high value substrates may warrant multiple additional processing steps to increase yield where the profit resulting from a higher yield outweighs the additional costs.

Various embodiments of the invention have been described above for purposes of illustrating the details thereof and to enable one of ordinary skill in the art to make and use the invention. The details and features of the disclosed embodiment[s] are not intended to be limiting, as many variations and modifications will be readily apparent to those of skill in the art. Accordingly, the scope of the present disclosure is intended to be interpreted broadly and to include all variations and modifications coming within the scope and spirit of the appended claims and their legal equivalents.

What is claimed is:

1. A method of inspecting a substrate, comprising:
    obtaining a monochromatic image of the substrate using fluorescent light emitted from the substrate, the substrate including a via;
    identifying whether the location of the via is also the location of an anomaly visible in the monochromatic image;
    reworking the substrate where the location of the via and the location of the anomaly coincide; and,
    inspecting again the substrate to determine whether the anomaly remains.

2. The method of inspecting a substrate of claim 1 further comprising:
  determining upon reinspection whether the substrate has been corrected and if not, determining whether the substrate may economically be reworked yet again.

3. The method of inspecting a substrate of claim 2 further comprising:
  scrapping the substrate if it cannot be economically be reworked.

4. A semiconductor device manufactured according to the method of claim 1.

5. A method of inspecting a substrate, comprising:
  obtaining an image of the substrate using fluorescent light emitted from the substrate, the substrate including a pillar;
  identifying whether the location of the pillar is also the location of an anomaly visible in the image;
  reworking the substrate where the location of the pillar and the location of the anomaly coincide; and
  inspecting again the substrate to determine whether the anomaly remains.

6. The method of inspecting a substrate of claim 5 further comprising:
  determining upon reinspection whether the substrate has been corrected and if not, determining whether the substrate may economically be reworked yet again.

7. The method of inspecting a substrate of claim 6 further comprising:
  scrapping the substrate where a cost associated with the substrate exceeds a predetermined threshold.

8. A semiconductor device manufactured according to the method of claim 4.

9. A method of inspecting a substrate, comprising:
  obtaining a monochromatic image of the substrate using fluorescent light emitted from the substrate at a first wavelength, the substrate including a region of interest;
  identifying in the monochromatic image of the substrate whether an anomaly is present in the region of interest based on an intensity of light emitted at the first wavelength of a feature within the region of interest;
  assessing the anomaly to determine whether one or more defect characteristics thresholds are exceeded; and
  dispositioning the substrate based at least in part on the assessing step.

10. The method of inspecting a substrate of claim 9 wherein the region of interest includes a feature selected from a group consisting of a via, a pillar, a bump, and a pad.

11. The method of inspecting a substrate of claim 9 further comprising:
  capturing a second image of the substrate using fluorescent light emitted from the substrate at a second wavelength that includes the region of interest;
  identifying in the second image of the substrate whether an anomaly is present in the region of interest based on an intensity of light at the second wavelength of a feature within the region of interest;
  assessing the anomaly to determine whether one or more defect characteristics thresholds are exceeded; and
  identifying a defect identified from the second image using the second wavelength as a different type of defect from one that is identified in the first image using the first wavelength.

12. A semiconductor device manufactured according to the method of claim 9.

13. A method of inspecting a substrate comprising:
  obtaining an image of the substrate using fluorescent light emitted from the substrate that includes a region of interest;
  performing a threshold operation on the image whereby each pixel of the image that has an intensity value above a selected magnitude is set to a high value and each pixel of the image of the image that has an intensity value below the selected magnitude is set to a low value; and
  identifying in the thresholded image of the substrate whether an anomaly is present in the region of interest.

14. The method of claim 13 wherein the identifying step comprises:
  generating a differential image as between the thresholded image and a corresponding comparator image.

15. The method of claim 13 wherein the identifying step further comprises:
  assessing an anomaly to determine whether a characteristic of the anomaly exceeds a selected limit such that it is considered to be a defect.

16. A semiconductor device manufactured according to the method of claim 13.

17. A method of inspecting a substrate, comprising:
  obtaining a first image of the substrate using fluorescent light emitted from the substrate at a first wavelength, the substrate including a region of interest;
  identifying in the first image whether a first anomaly is present in the region of interest based on an intensity of light at the first wavelength of a feature within the region of interest;
  capturing a second image of the substrate at a second wavelength that includes the region of interest;
  identifying in the second image whether a second anomaly is present in the region of interest based on an intensity of light at the second fluorescence wavelength of a feature within the region of interest;
  assessing the first anomaly and the second anomaly to determine whether one or more defect characteristics thresholds are exceeded;
  dispositioning the substrate based at least in part on the assessing step; and
  identifying a defect identified from the second image using the second wavelength as a different type of defect from one that is identified in the first image using the first wavelength.

* * * * *